United States Patent
McCarthy et al.

(10) Patent No.: US 10,099,209 B2
(45) Date of Patent: *Oct. 16, 2018

(54) ALUMINA BOUND CATALYST FOR SELECTIVE CONVERSION OF OXYGENATES TO AROMATICS

(71) Applicant: ExxonMobil Research and Engineering Company, Annandale, NJ (US)

(72) Inventors: Stephen J. McCarthy, Center Valley, PA (US); Rohit Vijay, Bridgewater, NJ (US); Brett Loveless, Maplewood, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 733 days.

This patent is subject to a terminal disclaimer.

(21) Appl. No.: 14/560,070

(22) Filed: Dec. 4, 2014

(65) Prior Publication Data

US 2015/0174562 A1    Jun. 25, 2015

Related U.S. Application Data

(60) Provisional application No. 61/918,994, filed on Dec. 20, 2013, provisional application No. 61/918,984, (Continued)

(51) Int. Cl.
| | |
|---|---|
| *B01J 29/06* | (2006.01) |
| *B01J 29/40* | (2006.01) |
| *B01J 35/10* | (2006.01) |
| *B01J 29/70* | (2006.01) |
| *B01J 23/06* | (2006.01) |
| *C07C 1/22* | (2006.01) |
| *B01J 27/14* | (2006.01) |
| *C07C 1/20* | (2006.01) |
| *C10G 3/00* | (2006.01) |
| *C10L 1/06* | (2006.01) |
| *B01J 38/02* | (2006.01) |
| *B01J 38/12* | (2006.01) |
| *B01J 21/04* | (2006.01) |

(Continued)

(52) U.S. Cl.
CPC ............. *B01J 29/405* (2013.01); *B01J 21/04* (2013.01); *B01J 23/06* (2013.01); *B01J 27/14* (2013.01); *B01J 29/061* (2013.01); *B01J 29/7049* (2013.01); *B01J 29/90* (2013.01); *B01J 35/10* (2013.01); *B01J 35/108* (2013.01); *B01J 35/109* (2013.01); *B01J 35/1014* (2013.01); *B01J 35/1019* (2013.01); *B01J 35/1023* (2013.01); *B01J 35/1057* (2013.01); *B01J 37/0201* (2013.01); *B01J 38/02* (2013.01); *B01J 38/12* (2013.01); *C07C 1/20* (2013.01); *C07C 1/22* (2013.01); *C10G 3/45* (2013.01); *C10G 3/49* (2013.01); *C10G 3/55* (2013.01); *C10L 1/06* (2013.01); *B01J 37/0009* (2013.01); *B01J 2229/186* (2013.01); *B01J 2229/20* (2013.01); *B01J 2229/42* (2013.01); *C07C 2523/06* (2013.01); *C07C 2529/40* (2013.01); *C07C 2529/70* (2013.01); *C10L 2200/0423* (2013.01); *C10L 2200/0469* (2013.01); *C10L 2270/023* (2013.01); *Y02P 20/584* (2015.11); *Y02P 30/20* (2015.11); *Y02P 30/42* (2015.11)

(58) Field of Classification Search
CPC .... B01J 29/405; B01J 29/061; B01J 35/1014; B01J 35/1019; B01J 35/10; B01J 35/108; B01J 35/109; B01J 35/1057; B01J 35/1061; B01J 37/0201; B01J 37/0009; B01J 2229/20; B01J 2229/186; B01J 2229/42
USPC ......................................... 502/64, 71, 77, 85
See application file for complete search history.

(56) References Cited

U.S. PATENT DOCUMENTS

| | | |
|---|---|---|
| 3,354,078 A | 11/1967 | Maile et al. |
| 3,702,886 A | 11/1972 | Argauer et al. |

(Continued)

FOREIGN PATENT DOCUMENTS

| | | |
|---|---|---|
| CN | 101602643 | 12/2009 |
| CN | 101602648 | 12/2009 |

(Continued)

OTHER PUBLICATIONS

Eastwood, S.C., et al., "Pilot Plants: Thermofor Catalytic Cracking Unit", Industrial and Engineering Chemistry, Dec. 1947, pp. 1685-1690, vol. 39, No. 12, ACS Publications.

(Continued)

*Primary Examiner* — Elizabeth D Wood
(74) *Attorney, Agent, or Firm* — Liza Negron

(57) ABSTRACT

A catalyst composition comprising a zeolite, an alumina binder, and a Group 12 transition metal selected from Zn and/or Cd, the zeolite having a Si/Al ratio of at least about 10 and a micropore surface area of at least about 340 m²/g, the catalyst composition comprising about 50 wt % or less of the binder, based on a total weight of the catalyst composition, and having a micropore surface area of at least about 290 m²/g, a molar ratio of Group 12 transition metal to aluminum of about 0.1 to about 1.3, and at least one of: a mesoporosity of about 20 m²/g to about 120 m²/g; a diffusivity for 2,2-dimethylbutane of greater than about $1\times10^{-2}$ sec$^{-1}$ when measured at a temperature of about 120° C. and a 2,2-dimethylbutane pressure of about 60 torr (8 kPa); and a combined micropore surface area and mesoporosity of at least about 380 m²/g.

16 Claims, No Drawings

Related U.S. Application Data filed on Dec. 20, 2013, provisional application No. 61/919,013, filed on Dec. 20, 2013.

(51) Int. Cl.
  *B01J 29/90* (2006.01)
  *B01J 37/02* (2006.01)
  *B01J 37/00* (2006.01)

(56) References Cited

U.S. PATENT DOCUMENTS

| | | |
|---|---|---|
| 3,709,979 A | 1/1973 | Chu |
| 3,760,024 A | 9/1973 | Cattanach |
| 3,832,449 A | 8/1974 | Rosinski et al. |
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |
| 3,928,483 A | 12/1975 | Chang et al. |
| 3,960,978 A | 6/1976 | Givens et al. |
| 4,012,245 A | 4/1977 | Plank et al. |
| 4,016,218 A | 4/1977 | Haag et al. |
| 4,021,502 A | 5/1977 | Plank et al. |
| 4,025,571 A | 5/1977 | Lago |
| 4,035,430 A | 7/1977 | Dwyer et al. |
| 4,046,685 A | 9/1977 | Bray |
| 4,049,573 A | 9/1977 | Kaeding |
| 4,058,576 A | 11/1977 | Chang et al. |
| 4,076,842 A | 2/1978 | Plank et al. |
| 4,079,095 A | 3/1978 | Givens et al. |
| 4,088,706 A | 5/1978 | Kaeding |
| RE29,948 E | 3/1979 | Dwyer et al. |
| 4,150,062 A | 4/1979 | Garwood et al. |
| 4,157,293 A | 6/1979 | Plank et al. |
| 4,211,640 A | 7/1980 | Garwood et al. |
| 4,227,992 A | 10/1980 | Garwood et al. |
| 4,288,645 A | 9/1981 | Wagstaff |
| 4,291,182 A | 9/1981 | Dautzenberg et al. |
| 4,326,994 A | 4/1982 | Haag et al. |
| 4,397,827 A | 8/1983 | Chu |
| 4,403,044 A | 9/1983 | Post et al. |
| 4,417,780 A | 11/1983 | Knapp |
| 4,423,274 A | 12/1983 | Daviuduk et al. |
| 4,433,185 A | 2/1984 | Tabak |
| 4,433,189 A | 2/1984 | Young |
| 4,450,311 A | 5/1984 | Wright et al. |
| 4,456,779 A | 6/1984 | Owen et al. |
| 4,538,017 A | 8/1985 | Butler et al. |
| 4,556,477 A | 12/1985 | Dwyer |
| 4,579,993 A | 4/1986 | Bowes et al. |
| 4,582,815 A | 4/1986 | Bowes |
| 4,584,423 A | 4/1986 | Nacamuli et al. |
| 4,590,321 A | 5/1986 | Chu |
| 4,621,161 A | 11/1986 | Shihabi |
| 4,628,135 A | 12/1986 | Owen et al. |
| 4,665,251 A | 5/1987 | Chu |
| 4,720,602 A | 1/1988 | Chu |
| 4,788,369 A | 11/1988 | Marsh et al. |
| 4,808,763 A | 2/1989 | Shum |
| 5,365,004 A | 11/1994 | Beck et al. |
| 5,367,099 A | 11/1994 | Beck et al. |
| 5,625,103 A | 4/1997 | Abichandani et al. |
| 5,633,417 A | 5/1997 | Beck et al. |
| 5,675,047 A | 10/1997 | Beck et al. |
| 5,705,726 A | 1/1998 | Abichandani et al. |
| 5,877,368 A | 3/1999 | Kiyama et al. |
| 5,883,034 A | 3/1999 | Drake et al. |
| 5,998,688 A | 12/1999 | Abichandani et al. |
| 6,028,238 A | 2/2000 | Beck et al. |
| 6,048,815 A | 4/2000 | Yao et al. |
| 6,156,689 A | 12/2000 | Kimble et al. |
| 6,177,374 B1 | 1/2001 | Pradhan et al. |
| 6,187,982 B1 | 2/2001 | Beck et al. |
| 6,372,680 B1 | 4/2002 | Wu et al. |
| 6,372,949 B1 | 4/2002 | Brown et al. |
| 6,417,421 B1 | 7/2002 | Yao |
| 6,423,879 B1 | 7/2002 | Brown et al. |
| 6,504,072 B1 | 1/2003 | Brown et al. |
| 7,285,511 B2 | 10/2007 | Ghosh et al. |
| 7,304,194 B2 | 12/2007 | Ghosh et al. |
| 7,453,018 B2 | 11/2008 | Dakka et al. |
| 7,722,825 B1 | 5/2010 | Bizzabi et al. |
| 7,799,962 B2 | 9/2010 | Dakka et al. |
| 2006/0161035 A1 | 7/2006 | Kalnes et al. |
| 2013/0123557 A1 | 5/2013 | McCarthy et al. |
| 2013/0158323 A1 | 6/2013 | Mondal |
| 2013/0165725 A1 | 6/2013 | Chewter et al. |
| 2013/0281753 A1 | 10/2013 | McCarthy et al. |
| 2013/0303814 A1 | 11/2013 | Mammadov et al. |
| 2014/0018592 A1 | 1/2014 | Chen et al. |

FOREIGN PATENT DOCUMENTS

| | | |
|---|---|---|
| CN | 101607864 | 12/2009 |
| CN | 101780417 | 7/2010 |
| CN | 101823929 | 9/2010 |
| EP | 123449 A1 | 10/1984 |
| EP | 172686 A1 | 2/1986 |
| WO | 9951549 A1 | 10/1999 |
| WO | 129152 A1 | 4/2001 |
| WO | 2005068406 A1 | 7/2005 |
| WO | 2006012150 A2 | 2/2006 |
| WO | 2009021726 A1 | 2/2009 |
| WO | 2013017497 A1 | 2/2013 |

OTHER PUBLICATIONS

Chang et al., "The Conversion of Methanol and Other O-Compounds to Hydrocarbons over Zeolite Catalysts", Journal of Catalysis, 1977, pp. 249-259, vol. 47, Academic Press.

Ono et al., "Selective conversion of methanol into aromatic hydrocarbons over zinc-exchanged ZSM-5 zeolites," Journal of the Chemical Society, Faraday Transactions 1, Jan. 1988, p. 1091, vol. 84, No. 4, Royal Society of Chemistry.

Wolterman, G.W., et al., "Chapter 4 Commercial Preparation and Characterization of FCC Catalysts", Studies in Surface Science and Catalysis, 1993, pp. 105-144, vol. 76, Elsevier.

Inque et al., "Selective conversion of methanol into aromatic hydrocarbons over silver-exchanged ZSM-5 zeolites," Microporous Materials, Aug. 1995, pp. 379-383, vol. 4, No. 5, Elsevier.

International Search Report and Written Opinion from PCT/US2014/068508 dated Feb. 17, 2015.

International Search Report and Written Opinion from PCT/US2014/068509 dated Feb. 25, 2015.

International Search Report and Written Opinion from PCT/US2014/068612 dated Feb. 23, 2015.

International Search Report and Written Opinion from PCT/US2014/068625 dated Mar. 4, 2015.

International Search Report and Written Opinion from PCT/US2014/068607 dated Mar. 5, 2015.

International Search Report and Written Opinion from PCT/US2014/068503 dated Apr. 1, 2015.

International Search Report and Written Opinion from PCT/US2014/068512 dated Apr. 1, 2015.

International Search Report and Written Opinion from PCT/US2014/068506 dated Apr. 8, 2015.

International Search Report and Written Opinion from PCT/US2014/068515 dated Apr. 10, 2015.

ALUMINA BOUND CATALYST FOR SELECTIVE CONVERSION OF OXYGENATES TO AROMATICS

CROSS-REFERENCE TO RELATED APPLICATIONS

This application claims the benefit of provisional U.S. Application Nos. 61/918,984, 61/918,994, and 61/919,013, each filed on Dec. 20, 2013; each of which are incorporated by reference herein in their entirety.

FIELD

This invention relates to catalysts for converting oxygenates to aromatics and methods for using such catalysts.

BACKGROUND

A variety of industrial processes are known for conversion of low boiling carbon-containing compounds to higher value products. For example, methanol to gasoline (MTG) is a commercial process that produces gasoline from methanol using ZSM-5 catalysts. In the MTG process, methanol is first dehydrated to dimethyl ether. The methanol and/or dimethyl ether then react in a series of reactions that result in formation of aromatic, paraffinic, and olefinic compounds. The resulting product consists of liquefied petroleum gas (LPG) and a high-quality gasoline comprised of aromatics, paraffins, and olefins. The typical MTG hydrocarbon product consists of about 40-50% aromatics plus olefins and about 50-60% paraffins.

U.S. Pat. Nos. 6,423,879 and 6,504,072 disclose a process for the selective production of para-xylene which comprises reacting toluene with methanol in the presence of a catalyst comprising a porous crystalline material having a diffusivity for 2,2-dimethylbutane of less than about $10^{-4}$ $sec^{-1}$ when measured at a temperature of about 120° C. and a 2,2-dimethylbutane pressure of about 60 torr (8 kPa). The porous crystalline material is preferably a medium-pore zeolite, particularly ZSM-5, which has been severely steamed at a temperature of at least about 950° C. and which has been combined with about 0.05 to about 20 wt % of at least one oxide modifier, preferably an oxide of phosphorus, to control reduction of the micropore volume of the material during the steaming step. The porous crystalline material is normally combined with a binder or matrix material, preferably silica or a kaolin clay.

U.S. Pat. No. 4,088,706 describes a method for converting methanol to para-xylene. The method includes exposing a feed to a zeolite catalyst that is modified to include boron and/or magnesium.

U.S. Pat. No. 4,584,423 describes a method for xylene isomerization using a preferably alumina-bound zeolite catalyst containing a Group 2 or Group 12 metal. A feed containing a mixture of aromatic compounds including ethylbenzene is exposed to the catalyst for conversion of ethylbenzene to other compounds while reducing or minimizing the amount of xylene conversion.

U.S. Pat. No. 3,894,104 describes a method for converting oxygenates to aromatics using zeolite catalysts impregnated with a transition metal. Yields of aromatics relative to the total hydrocarbon product are reported to be as high as about 58% with a corresponding total C5+ yield as high as about 73%.

U.S. Patent Application Publication No. 2013/0281753 describes a phosphorous modified zeolite catalyst. The phosphorous modification reduces the change in alpha value for the catalyst after the catalyst is exposed to an environment containing steam. The phosphorous modified catalysts are described as being suitable, for example, for conversion of methanol to gasoline boiling range compounds.

SUMMARY

In one aspect, a catalyst composition is provided to include a zeolite, an alumina binder, and a Group 12 transition metal selected from the group consisting of Zn, Cd, or a combination thereof, the zeolite having a silicon to aluminum ratio of at least about 10, the zeolite having a micropore surface area of at least about 340 $m^2/g$, such as at least about 350 $m^2/g$, or at least about 370 $m^2/g$, or at least about 380 $m^2/g$, the catalyst composition comprising about 80 wt % or less of the binder based on a total weight of the catalyst composition, and the catalyst composition having a micropore surface area of at least about 290 $m^2/g$, a molar ratio of Group 12 transition metal to aluminum of about 0.1 to about 1.3, and at least one of: (a) a mesoporosity of about 20 $m^2/g$ to about 120 $m^2/g$; (b) a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa); and (c) a combined micropore surface area and mesoporosity of at least about 380 $m^2/g$, such as greater than about 390 $m^2/g$.

In another aspect, a catalyst composition is provided to include a zeolite, an alumina binder, and a Group 12 transition metal selected from the group consisting of Zn, Cd, or a combination thereof, the zeolite having a silicon to aluminum ratio of at least about 20, the zeolite having a micropore surface area of at least about 340 $m^2/g$, the catalyst composition comprising about 50 wt % or less of the binder based on a total weight of the catalyst composition, and the catalyst composition having a micropore surface area of at least about 290 $m^2/g$, a molar ratio of Group 12 transition metal to aluminum of about 0.1 to about 1.3, a mesoporosity of about 20 $m^2/g$ to about 120 $m^2/g$, a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa), and a combined micropore surface area and mesoporosity of at least about 380 $m^2/g$.

DETAILED DESCRIPTION OF THE PREFERRED EMBODIMENTS

Aromatics and olefins are valuable chemical products. Although processes for converting methanol to gasoline are known, such processes may not enhance or maximize the production of valuable aromatics and/or olefins. Thus, a catalyst or process that can further increases the amount of aromatic and/or olefinic products generated from conversion of methanol or other oxygenates, while minimizing paraffin formation, could be commercially attractive.

In various aspects, catalysts described herein can be used to convert an oxygenate feed into aromatics and/or olefins with improved yield of one or more desired components relative to the total hydrocarbon product generated in the conversion reaction. The total hydrocarbon product from an oxygenate conversion reaction is defined as the yield of hydrocarbon or hydrocarbonaceous products. Thus, the yield of compounds such as water, coke, or other non-hydrocarbonaceous products is excluded from the total hydrocarbon yield. The improved yield can be identified as an improved yield of aromatics relative to the total hydrocarbon product; an improved combined yield of aromatics and olefins relative to the total hydrocarbon product; an improved yield of aromatics relative to the yield of C5+ (liquid) product in the total hydrocarbon product; or a combination thereof.

In addition to improved yield, the catalysts described herein can also be bound using alumina. Alumina is a commonly used binder for formulating zeolite catalysts. This is due in part to the ease of use of alumina as a binder material. However, for some types of zeolite catalyst applications, alumina has previously been known to reduce zeolite catalytic activity. It has unexpectedly been determined that any reduction in activity due to use of an alumina binder can be mitigated and/or minimized by using a low surface area alumina binder. Without being bound by any particular theory, it is believed that low surface area alumina binders can provide several benefits when used for formulation of a transition metal-enhanced catalyst. First, use of a low surface area alumina binder can reduce and/or minimize the loss of micropore surface area when formulating a bound catalyst. The zeolite crystals described herein preferably have a micropore surface area of at least about 340 m$^2$/g. Formulating such zeolite crystals into a catalyst with an alumina binder can lead to formation of catalyst particles with substantially lower micropore surface area. However, by using a low surface area alumina binder, the resulting micropore surface of an alumina bound catalyst can be more comparable to the micropore surface area of the zeolite crystals. Additionally, using a low surface area alumina binder is believed to provide less surface area for migration of the transition metal from the zeolite to the binder.

One example of the difficulties in using conventional catalysts for converting oxygenates, such as methanol, to gasoline (MTG) is the formation of substantial amounts of paraffins in the liquid hydrocarbon product. C5+ paraffins, such as C5-C8 paraffins, are an acceptable component in a conventional naphtha or gasoline product. However, although such paraffins are acceptable, C5-C8 paraffins are otherwise typically a relatively low value product. Generation of lower value products from a catalyzed synthesis process reduces the overall value of the process.

In contrast to conventional methods, conversion of oxygenates using catalysts as described herein (such as catalysts bound using a low surface area binder) can enhance the relative amount of aromatics and olefins generated during conversion. In other words, the amount of paraffins generated in the total hydrocarbon product can be reduced, and/or the amount of paraffins in the liquid portion (C5+) of the hydrocarbon product can be reduced.

The enhanced yield of desirable products can be identified in several ways. One way of identifying the enhanced yield of desirable products is to consider either the amount of aromatics produced relative to the total hydrocarbon product, or to consider the aromatics plus olefins produced in the total hydrocarbon product. Increasing the amount of aromatics generated can indicate production of higher value components based on the value of various aromatic compounds for applications other than as a fuel. Typically aromatics are produced as a mixture of aromatics having various numbers of carbon atoms. Performing a separation on the mixture of aromatics can allow for recovery of the higher value aromatics in the mixture.

Increasing the combined amount of aromatics and olefins can also indicate an increase in the value of the products generated from a reaction. At least part of the olefins generated in the total hydrocarbon product can correspond to C2-C4 olefins. These olefins can be suitable for use as raw materials for a variety of polymer synthesis reactions. Thus, even though the increase in chain length for C2-C4 olefins is small relative to an initial methanol feed, such C2-C4 olefins can still represent a higher value product than paraffins generated by conversion of methanol (or another oxygenate).

As an alternative to using the combined amount of aromatics plus olefins, the amount of aromatics generated relative to the liquid yield of the total hydrocarbon product can also indicate production of a higher value mixture of products. The liquid portion or yield for the hydrocarbon products typically refers to the portion of the hydrocarbon products that contain at least 5 carbons (C5+ compounds). The difference between the weight percent of aromatics in the total hydrocarbon product versus the weight percent of liquid product in the total hydrocarbon product usually corresponds to paraffinic compounds. Thus, reducing and/or minimizing the amount of difference between the liquid product yield and the aromatic product yield can correspond to production of a higher value mixture of hydrocarbon products.

Catalyst for Oxygenate to Aromatics Conversion

In various aspects, a transition metal-enhanced zeolite catalyst composition is provided, along with methods for use of the transition metal enhanced catalyst for conversion of oxygenate feeds to aromatics and olefins with enhanced overall yield and/or enhanced aromatics yield. In some cases, the present catalyst composition is alternatively referred to as being self-bound. The terms "unbound" and "self-bound" are intended to be synonymous and mean that the present catalyst composition is free of any of the inorganic oxide binders, such as alumina or silica, frequently combined with zeolite catalysts to enhance their physical properties.

The zeolite employed in the present catalyst composition generally comprises at least one medium pore aluminosilicate zeolite having a Constraint Index of 1-12 (as defined in U.S. Pat. No. 4,016,218). Suitable zeolites include zeolites having an MFI or MEL framework, such as ZSM-5 or ZSM-11. ZSM-5 is described in detail in U.S. Pat. No. 3,702,886 and RE 29,948. ZSM-11 is described in detail in U.S. Pat. No. 3,709,979. Preferably, the zeolite is ZSM-5.

Generally, a zeolite having the desired activity can have a silicon to aluminum molar ratio of about 10 to about 300, such as about 15 to about 100 or about 20 to about 40. For example, the silicon to aluminum ratio can be at least about 10, such as at least about 20, at least about 30, at least about 40, at least about 50, or at least about 60. Additionally or alternately, the silicon to aluminum ratio can be about 300 or less, such as about 200 or less, about 100 or less, about 80 or less, about 60 or less, or about 50 or less.

In some preferred aspects, the silicon to aluminum ratio can be at least about 20, such as at least about 30 or at least about 40. In such embodiments, the silicon to aluminum ratio can optionally be about 80 or less, such as about 60 or less, about 50 or less, or about 40 or less. Typically, reducing the silicon to aluminum ratio in a zeolite can result in a zeolite with a higher acidity, and therefore higher activity for cracking of hydrocarbon or hydrocarbonaceous feeds, such as petroleum feeds. However, with respect to conversion of oxygenates to aromatics, such increased cracking activity may not be beneficial, and instead may result in increased formation of residual carbon or coke during the conversion reaction. Such residual carbon can deposit on the zeolite catalyst, leading to deactivation of the catalyst over time. Having a silicon to aluminum ratio of at least about 40, such as at least about 50 or at least about 60, can reduce and/or minimize the amount of additional residual carbon formed due to the acidic or cracking activity of the catalyst.

It is noted that the molar ratio described herein is a ratio of silicon to aluminum. If a corresponding ratio of silica to alumina were described, the corresponding ratio of silica (SiO$_2$) to alumina (Al$_2$O$_3$) would be twice as large, due to the presence of two aluminum atoms in each alumina stoichiometric unit. Thus, a silicon to aluminum ratio of 10 corresponds to a silica to alumina ratio of 20.

When used in the present catalyst composition, the zeolite can be present at least partly in the hydrogen (acid) form. Depending on the conditions used to synthesize the zeolite, this may correspond to converting the zeolite from, for example, the alkali metal (sodium) ion form. This can readily be achieved, for example, by ion exchange to convert the zeolite to the ammonium form followed by calcination in an oxidizing atmosphere (air) or an inert atmosphere at a temperature of about 400° C. to about 700° C. to convert the ammonium form to the active hydrogen form.

Additionally or alternately, the catalyst composition can include and/or be enhanced by a transition metal. Preferably the transition metal is a Group 12 metal from the IUPAC periodic table (sometimes designated as Group IIB) selected from Zn and/or Cd. The transition metal can be incorporated into the zeolite by any convenient method, such as by impregnation or by ion exchange. After impregnation or ion exchange, the transition metal-enhanced catalyst can be treated in oxidizing (air) or inert atmosphere at a temperature of about 400° C. to about 700° C. The amount of transition metal can be related to the molar amount of aluminum present in the zeolite. Preferably, the molar amount of the transition metal can correspond to about 0.1 to about 1.3 times the molar amount of aluminum in the zeolite. For example, the molar amount of transition metal can be about 0.1 times the molar amount of aluminum in the zeolite, such as at least about 0.2 times, at least about 0.3 times, or at least about 0.4 times. Additionally or alternately, the molar amount of transition metal can be about 1.3 times or less relative to the molar amount of aluminum in the zeolite, such as about 1.2 times or less, about 1.0 times or less, or about 0.8 times or less. Still further additionally or alternately, the amount of transition metal can be expressed as a weight percentage of the bound zeolite catalyst, such as having at least about 0.1 wt % of transition metal, at least about 0.25 wt %, at least about 0.5 wt %, at least about 0.75 wt %, or at least about 1.0 wt %. Additionally or alternately, the amount of transition metal can be about 20 wt % or less, such as about 10 wt % or less, about 5 wt % or less, about 2.0 wt % or less, about 1.5 wt % or less, about 1.2 wt % or less, about 1.1 wt % or less, or about 1.0 wt % or less.

Additionally or alternately, the catalyst composition can be substantially free of phosphorous. A catalyst composition that is substantially free of phosphorous can contain about 0.01 wt % of phosphorous or less, such as less than about 0.005 wt % or less than about 0.001 wt %. A catalyst composition that is substantially free of phosphorous can be substantially free of intentionally added phosphorous or substantially free of both intentionally added phosphorous as well as phosphorous present as an impurity in a reagent for forming the catalyst composition. Additionally or alternately, the catalyst composition can contain no added phosphorous, such as containing no intentionally added phosphorous and/or containing no phosphorous impurities to within the detection limits of standard methods for characterizing a reagent and/or a resulting zeolite.

The transition metal-enhanced zeolite catalyst composition employed herein can further be characterized by at least one, for example at least two or all, of the following properties: (a) a mesoporosity of greater than about 20 m$^2$/g, such as greater than about 30 m$^2$/g, and less than about 120 m$^2$/g, such as less than about 100 m$^2$/g or less than about 85 m$^2$/g; (b) a microporous surface area of at least about 290 m$^2$/g, such as at least about 300 m$^2$/g or at least about 310 m$^2$/g; and (c) a diffusivity for 2,2-dimethylbutane of greater than about $1.0\times10^{-2}$ sec$^{-1}$, such as greater than about $1.25\times10^{-2}$ sec$^{-1}$, when measured at a temperature of about 120° C. and a 2,2-dimethylbutane pressure of about 60 torr (about 8 kPa). Additionally or alternately, a bound catalyst composition can have a combined micropore and mesopore surface area of at least about 380 m$^2$/g, such as at least about 390 m$^2$/g.

Of these properties, mesoporosity and diffusivity for 2,2-dimethylbutane can be determined by a number of factors for a given zeolite, including the crystal size of the zeolite. Microporous surface area can be determined by the pore size of the zeolite and the availability of the zeolite pores at the surfaces of the catalyst particles. Producing a zeolite catalyst with the desired minimum mesoporosity, microporous surface area, and 2,2-dimethylbutane diffusivity would be well within the expertise of anyone of ordinary skill in zeolite chemistry. It is noted that mesopore (and/or external) surface area and micropore surface area can be characterized, for example, using adsorption-desorption isotherm techniques within the expertise of one of skill in the art, such as the BET (Brunauer Emmet Teller) method.

It is noted that the micropore surface area can be characterized for zeolite crystals and/or for a catalyst formed from the zeolite crystals. In various aspects, the micropore surface area of a self-bound catalyst and/or a catalyst formulated with a separate binder can be at least about 340 m$^2$/g, such as at least about 350 m$^2$/g, at least about 370 m$^2$/g, or at least about 380 m$^2$/g. Typically, a formulation of zeolite crystals into catalyst particles (either self-bound or with a separate binder) can result in some loss of micropore surface area relative to the micropore surface area of the zeolite crystals. Thus, in order to provide a catalyst having the desired micropore surface area, the zeolite crystals can also have a micropore surface area of at least about 340 m$^2$/g, such as at least about 350 m$^2$/g, at least about 360 m$^2$/g, at least about 370 m$^2$/g, or at least about 380 m$^2$/g. As a practical matter, the micropore surface area of a zeolite crystal and/or a corresponding self-bound or bound catalyst as described herein can be less than about 1000 m$^2$/g, and typically less than about 750 m$^2$/g. Additionally or alternately, the micropore surface area of a catalyst (self-bound or with a separate binder) can be about 105% or less of the micropore surface area of the zeolite crystals in the catalyst, and typically about 100% or less of the micropore surface area of the zeolite crystals in the catalyst, such as from about 80% to 100% of the micropore surface area of the zeolite crystals in the catalyst. For example, the micropore surface area of a catalyst can be at least about 80% of the micropore surface area of the zeolite crystals in the catalyst, such as at least about 85%, at least about 90%, at least about 95%, at least about 97%, or at least about 98%, and/or about 100% or less, about 99% or less, about 98% or less, about 97% or less, or about 95% or less.

Additionally or alternately, the diffusivity for 2,2-dimethylbutane of a catalyst (self-bound or with a separate binder) can be about 105% or less of the diffusivity for 2,2-dimethylbutane of the zeolite crystals in the catalyst, and typically about 100% or less of the diffusivity for 2,2-dimethylbutane of the zeolite crystals in the catalyst, such as from about 80% to 100% of the diffusivity for 2,2-dimethylbutane of the zeolite crystals in the catalyst. For example, the diffusivity for 2,2-dimethylbutane of a catalyst can be at least about 80% of the diffusivity for 2,2-dimethylbutane of the zeolite crystals in the catalyst, such as at least about 85%, at least about 90%, at least about 95%, at least about 97%, or at least about 98%, and/or about 100% or less, about 99% or less, about 98% or less, about 97% or less, or about 95% or less.

In some aspects, the zeolite catalyst can have an alpha value of at least about 10, such as at least about 20 or at least about 50. Alpha value is a measure of the acid activity of a zeolite catalyst as compared with a standard silica-alumina catalyst. The alpha test is described in U.S. Pat. No. 3,354,078; in the Journal of Catalysis at vol. 4, p. 527 (1965), vol. 6, p. 278 (1966), and vol. 61, p. 395 (1980), each incorporated herein by reference as to that description. The experimental conditions of the test used herein include a constant temperature of about 538° C. and a variable flow rate as described in detail in the Journal of Catalysis at vol. 61, p. 395. The higher alpha values can typically correspond with a more active cracking catalyst.

Catalyst Binders

A catalyst composition as described herein can employ a transition metal-enhanced zeolite in its original crystalline form, or the crystals can be formulated into catalyst particles, such as by extrusion. One example of binding zeolite crystals to form catalyst particles is to form a self-bound catalyst. A process for producing zeolite extrudates in the absence of a binder is disclosed in, for example, U.S. Pat. No. 4,582,815, the entire contents of which are incorporated herein by reference.

As another example of forming a self-bound catalyst, the following procedure describes a representative method for forming self-bound ZSM-5 catalyst particles. It is noted that the absolute values in grams provided below should be considered as representative of using an appropriate ratio of the various components. ZSM-5 crystal (such as about 1,400 grams on a solids basis) can be added to a mixer and dry mulled. Then, approximately 190 grams of deionized water can be added during mulling. After about 10 minutes, about 28 grams of about 50 wt % caustic solution mixed with about 450 grams of deionized water can be added to the mixture and mulled for an additional about 5 minutes. The mixture can then be extruded into ~1/10" quadralobes. The extrudates can be dried overnight at about 250° F. (about 121° C.) and then calcined in nitrogen for about 3 hours at about 1000° F. (about 538° C.). The extrudates can then be exchanged twice with an ~1N solution of ammonium nitrate. The exchanged crystal can be dried overnight at about 250° F. (about 121° C.) and then calcined in air for about 3 hours at about 1000° F. (about 538° C.). This can result in self-bound catalyst. Based on the exchange with ammonium nitrate and subsequent calcinations in air, the ZSM-5 crystals in such a self-bound catalyst can correspond to ZSM-5 with primarily hydrogen atoms at the ion exchange sites in the zeolite. Thus, such a self-bound catalyst is sometimes described as being a self-bound catalyst that can include H-ZSM-5.

To form a transition metal-enhanced catalyst, a self-bound catalyst as described above can be impregnated via incipient wetness with a solution containing the desired metal for impregnation, such as Zn and/or Cd. (Other methods for incorporating a transition metal into the catalyst, such as ion exchange, can be used in place of or in addition to such an impregnation.) The impregnated crystal can then be dried overnight at about 250° F. (about 121° C.), followed by calcination in air for about 3 hours at about 1000° F. (about 538° C.). More generally, a transition metal can be incorporated into the ZSM-5 crystals and/or catalyst at any convenient time, such as before or after ion exchange to form H-ZSM-5 crystals, or before or after formation of a self-bound extrudate.

As an alternative to forming self-bound catalysts, zeolite crystals can be combined with a binder to form bound catalysts. Suitable binders for zeolite-based can include various inorganic oxides, such as silica, alumina, zirconia, titania, silica-alumina, or combinations thereof. Generally, a binder can be present in an amount between about 1 wt % and about 80 wt %, for example between about 5 wt % and about 40 wt % of a catalyst composition. In some aspects, the catalyst can include at least about 5 wt % binder, such as at least about 10 wt % or at least about 20 wt %. Additionally or alternately, the catalyst can include about 80 wt % or less of binder, such as about 50 wt % or less, about 40 wt % or less, or about 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, in U.S. Pat. No. 4,582,815. Optionally, a bound catalyst can be steamed after extrusion.

In some aspects, a binder for formulating a catalyst can be selected so that the resulting bound catalyst has a micropore surface area of at least about 290 $m^2/g$, such as at least about 300 $m^2/g$ or at least about 310 $m^2/g$. An example of a suitable binder for forming bound catalysts with a desirable micropore surface area is an alumina binder. Optionally but preferably, a suitable binder can be a binder with a surface area of about 200 $m^2/g$ or less, such as about 175 $m^2/g$ or less or about 150 $m^2/g$ or less. Unless otherwise specified, the surface area of the binder is defined herein as the combined micropore surface area and mesopore surface area of the binder.

As an example of forming a bound catalyst, the following procedure describes a representative method for forming alumina bound ZSM-5 catalyst particles. ZSM-5 crystal and an alumina binder, such as an alumina binder having a surface area of about 200 $m^2/g$ or less, can be added to a mixer and mulled. Additional deionized water can be added during mulling to achieve a desired solids content for extrusion. Optionally, a caustic solution can also be added to the mixture and mulled. The mixture can then be extruded into a desired shape, such as ~1/10" quadralobes. The extrudates can be dried overnight at about 250° F. (about 121° C.) and then calcined in nitrogen for about 3 hours at about 1000° F. (about 538° C.). The extrudates can then be exchanged twice with an ~1N solution of ammonium nitrate. The exchanged crystal can be dried overnight at about 250° F. (about 121° C.) and then calcined in air for about 3 hours at about 1000° F. (about 538° C.). This can result in an alumina bound catalyst. Based on the exchange with ammonium nitrate and subsequent calcinations in air, the ZSM-5 crystals in such a bound catalyst can correspond to ZSM-5 with primarily hydrogen atoms at the ion exchange sites in the zeolite. Thus, such a bound catalyst is sometimes described as being a bound catalyst that can include H-ZSM-5.

To form a transition metal-enhanced catalyst, a bound catalyst can be impregnated via incipient wetness with a solution containing the desired metal for impregnation, such as Zn and/or Cd. The impregnated crystal can then be dried overnight at about 250° F. (about 121° C.), followed by calcination in air for about 3 hours at about 1000° F. (about 538° C.). More generally, a transition metal can be incorporated into the ZSM-5 crystals and/or catalyst at any convenient time, such as before or after ion exchange to form H-ZSM-5 crystals, or before or after formation of a bound extrudate. In some aspects that are preferred from a standpoint of facilitating manufacture of a bound zeolite catalyst, the transition metal can be incorporated into the bound catalyst (such as by impregnation or ion exchange) after formation of the bound catalyst by extrusion or another convenient method.

Feedstocks and Products

In various aspects, catalysts described herein can be used for conversion of oxygenate feeds to aromatics and/or olefins products, such as oxygenates containing at least one C1-C4 alkyl group (e.g., oxygenates containing at least one C1-C3 alkyl group). Examples of suitable oxygenates include feeds containing methanol, dimethyl ether, C1-C4 alcohols, ethers with C1-C4 alkyl chains, including both asymmetric ethers containing C1-C4 alkyl chains (such as methyl ethyl ether, propyl butyl ether, or methyl propyl ether) and symmetric ethers (such as diethyl ether, dipropyl ether, or dibutyl ether), or combinations thereof. It is noted that oxygenates containing at least one C1-C4 alkyl group are intended to explicitly identify oxygenates having alkyl groups containing about 4 carbons or less. Preferably the oxygenate feed can include at least about 50 wt % of one or more suitable oxygenates, such as at least about 75 wt %, at least about 90 wt %, or at least about 95 wt %. Additionally or alternately, the oxygenate feed can include at least about 50 wt % methanol, such as at least about 75 wt % methanol, at least about 90 wt % methanol, or at least about 95 wt % methanol. The oxygenate feed can be derived from any convenient source. For example, the oxygenate feed can be formed by reforming of hydrocarbons in a natural gas feed to form synthesis gas ($H_2$, CO, $CO_2$), and then using the synthesis gas to form alcohols.

In yet other aspects, converting an oxygenate feed to aromatics in the presence of a catalyst as described herein can reduce and/or minimize the amount of coke formation that occurs during conversion.

Suitable and/or effective conditions for performing a conversion reaction can include temperatures between about 150° C. to about 550° C., total pressures between about 0.1 psia (about 0.7 kPaa) to about 500 psia (about 3.5 MPaa), and an oxygenate space velocity between about 0.1 $h^{-1}$ to about 20 $h^{-1}$, based on weight of oxygenate relative to weight of catalyst. For example, the temperature can be at least about 375° C., such as at least about 400° C., at least about 450° C., or at least about 460° C. Additionally or alternately, the temperature can be about 550° C. or less, such as about 525° C. or less or about 500° C. or less.

It is noted that the oxygenate feed and/or conversion reaction environment can include water in various proportions. Conversion of oxygenates to aromatics and olefins can result in production of water as a product, so the relative amounts of oxygenate (such as methanol or dimethyl ether) and water can vary within the reaction environment. Based on the temperatures present during methanol conversion, the water in the reaction environment can result in "steaming" of a catalyst. Thus, a catalyst used for conversion of oxygenates to aromatics can preferably include or be a catalyst that substantially retains activity when steamed. Water may also be present in a feed prior to contacting the zeolite catalyst. For example, in commercial processing of methanol to form gasoline, in order to control heat release within a reactor, an initial catalyst stage may be used to convert a portion of the methanol in a feed to dimethyl ether and water prior to contacting a zeolite catalyst for forming gasoline.

ADDITIONAL EMBODIMENTS

Embodiment 1

A catalyst composition comprising a zeolite, an alumina binder, and a Group 12 transition metal selected from the group consisting of Zn, Cd, or a combination thereof, the zeolite having a silicon to aluminum ratio of at least about 10, such as at least about 20, at least about 30, or at least about 40, the zeolite having a micropore surface area of at least about 340 $m^2/g$, such as at least about 350 $m^2/g$, at least about 370 $m^2/g$, or at least about 380 $m^2/g$, the catalyst composition comprising about 50 wt % or less of the binder based on a total weight of the catalyst composition, and the catalyst composition having a micropore surface area of at least about 290 $m^2/g$, a molar ratio of Group 12 transition metal to aluminum of about 0.1 to about 1.3, and at least one of: (a) a mesoporosity of about 20 $m^2/g$ to about 120 $m^2/g$; (b) a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa); and (c) a combined micropore surface area and mesoporosity of at least about 380 $m^2/g$, such as greater than about 390 $m^2/g$.

Embodiment 2

The catalyst composition of Embodiment 1, wherein the binder has a surface area of about 200 $m^2/g$ or less, such as about 175 $m^2/g$ or less or about 150 $m^2/g$ or less.

Embodiment 3

The catalyst composition of any of the above embodiments, wherein the catalyst composition comprises from about 5 wt % to about 40 wt % binder based on the total weight of the catalyst composition.

Embodiment 4

The catalyst composition of any of the above embodiments, wherein the catalyst composition has a microporous surface area of at least about 300 $m^2/g$, such as at least about 310 $m^2/g$.

Embodiment 5

The catalyst composition of any of the above embodiments, wherein the catalyst composition has a diffusivity for 2,2-dimethylbutane of greater than about $1.25 \times 10^{-2}$ $sec^{-1}$ when measured at a temperature of about 120° C. and a 2,2-dimethylbutane pressure of about 60 torr (about 8 kPa), such as greater than about $1.5 \times 10^{-2}$ $sec^{-1}$.

Embodiment 6

The catalyst composition of any of the above embodiments, wherein the catalyst composition has a mesoporosity of greater than about 30 $m^2/g$.

Embodiment 7

The catalyst composition of any of the above embodiments, wherein the zeolite has a constraint index of about 1 to about 12.

Embodiment 8

The catalyst composition of any of the above embodiments, wherein the zeolite comprises ZSM-5, ZSM-11, a zeolite having an MFI framework, a zeolite having an MEL framework, or a combination thereof.

Embodiment 9

The catalyst composition of any of the above embodiments, wherein the zeolite is ZSM-5.

Embodiment 10

The catalyst composition of any of embodiments 1-8, wherein the zeolite is ZSM-11.

Embodiment 11

The catalyst composition of any of the above embodiments, wherein the silicon to aluminum molar ratio of the zeolite is from about 20 to about 100, such as at least about 30 or at least about 40, and/or about 80 or less, about 60 or less, or about 50 or less.

Embodiment 12

The catalyst composition of any of the above embodiments, wherein the amount of Group 12 transition metal is about 0.1 wt % to about 20 wt % of the total catalyst composition, such as at least about 0.5 wt %, about 5 wt % or less, and/or about 2 wt % or less.

Embodiment 13

The catalyst composition of any of the above embodiments, wherein the catalyst composition has a mesoporosity of about 20 $m^2/g$ to about 120 $m^2/g$, a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa), and a combined micropore surface area and mesoporosity of at least about 380 $m^2/g$.

Embodiment 14

The catalyst composition of any of the above embodiments, wherein the catalyst composition has an alpha value of at least about 10, such as at least about 20 or at least about 50.

Embodiment 15

A process for organic compound conversion employing the catalyst composition of any of Embodiments 1-14, the process preferably comprising the conversion of oxygenates containing at least one C1-C4 alkyl group to aromatics, the oxygenates containing at least one C1-C4 alkyl group preferably comprising at least one of methanol, dimethyl ether, symmetric ethers containing C1-C4 alkyl groups, asymmetric ethers containing C1-C4 alkyl groups, C1-C4 alcohols, or a combination thereof.

EXAMPLES

The following examples show data from testing and analysis of a variety of ZSM-5 self-bound and alumina bound catalysts that were used for performing a methanol to aromatics reaction. Unless otherwise specified, after forming ZSM-5 crystals with a desired micropore surface area, the crystals were formed into self-bound or alumina-bound catalyst particles using procedures similar to those previously described.

In these Examples below, references to the micropore surface area of a catalyst correspond to the micropore surface area of a bound catalyst, such as a self-bound catalyst or an alumina-bound catalyst. For a self-bound catalyst, the procedure for self-binding may cause some reduction in micropore surface area of the catalyst relative to the micropore surface area of the corresponding zeolite crystals prior to self-binding. Similarly, using an additional binder is expected to produce a catalyst with a lower microporous surface area than the microporous surface area of the zeolite crystals.

For catalysts described in the Examples, the following is a representative procedure for formation of ZSM-5 crystals. It is noted that the absolute values in grams provided below should be considered as representative of using an appropriate ratio of the various components. ZSM-5 crystal (about 1,400 grams on a solids basis) was added to a mixer and dry mulled. Then, approximately 190 grams of deionized water was added during mulling. After about 10 minutes, about 28 grams of about 50 wt % caustic solution mixed with about 450 grams of deionized water were added to the mixture and mulled for an additional about 5 minutes. The mixture was then extruded into ~1/10" quadralobes. The extrudates were dried overnight at about 250° F. (about 121° C.) and then calcined in nitrogen for about 3 hours at about 1000° F. (about 538° C.). The extrudates were then exchanged twice with an about 1N solution of ammonium nitrate. The exchanged crystal was dried overnight at about 250° F. (about 121° C.) and then calcined in air for about 3 hours at about 1000° F. (about 538° C.).

In the following examples, some of the ZSM-5 catalysts include a transition metal, such as Zn and/or Cd. To form the transition metal-enhanced catalysts described below, a self-bound catalyst or bound catalyst as described above was impregnated via incipient wetness with a solution containing the desired metal for impregnation. The impregnated crystal was then dried overnight at about 250° F. (about 121° C.) and then calcined in air for about 3 hours at about 1000° F. (about 538° C.).

Example 1—Micropore Surface Area Versus Aromatics Yield

In various aspects, suitable methanol conversion catalysts can have sufficient microporous surface area, such as a micropore surface area of at least about 340 $m^2/g$, such as at least about 350 $m^2/g$. Micropore surface areas of six example ZSM-5 catalysts, all with about 0.85-1 wt % Zn, are shown in Table 1. The aromatic content (wt % of hydrocarbon product) during methanol conversion at about 450° C., an inlet feed pressure of about 15 psig (about 110 kPag) and about 20 WHSV (g-$CH_3OH$ g-$catalyst^{-1}$ $h^{-1}$) is also shown in Table 1. The inlet feed was a mixture of methanol and water, to provide about 13.5 psig (about 95 kPag) of $CH_3OH$ and about 1.5 psig (about 11 kPag) of $H_2O$. The reaction conditions used for methanol conversion in Table 1 resulted in substantially complete conversion of the methanol in the feed. Unless otherwise indicated, the methanol conversion reactions were performed in a tubular stainless steel reactor. Note that in Table 1 (as well as tables in the other Examples), the ZSM-5 is described in terms of a ratio of Si to $Al_2$. The corresponding silicon to aluminum ratio is half of the value of the Si to $Al_2$ ratio.

For the catalysts in Table 1, all of the catalysts correspond to self-bound catalysts. As shown in Table 1, the resulting aromatics weight percent in the total hydrocarbon product appear to be strongly correlated with the micropore surface area, although other factors can also influence the final amount of aromatics in the hydrocarbon product.

TABLE 1

Micropore Surface Area versus Aromatics Yield

| Catalyst | Si/Al$_2$ | Micropore Surface Area (m$^2$/g) | Aromatics (wt %) in hydrocarbon product |
|---|---|---|---|
| Zn/H-ZSM-5 | ~60 | ~193 | ~31 |
| Zn/H-ZSM-5 | ~60 | ~218 | ~29 |
| Zn/H-ZSM-5 | ~60 | ~277 | ~34 |
| Zn/H-ZSM-5 | ~60 | ~375 | ~54 |
| Zn/H-ZSM-5 | ~60 | ~376 | ~57 |
| Zn/H-ZSM-5 | ~60 | ~383 | ~54 |

Example 2—Micropore Surface Area Versus Aromatics Yield

Example 1 demonstrated the impact of micropore surface area on aromatics production for various Zn/H-ZSM-5 catalysts. In this example, the impact of including Zn as a transition metal was demonstrated. Table 2 shows the methanol to aromatics selectivity for ZSM-5 catalysts of different micropore surface area, with and without added Zn. As shown in Table 2, aromatic selectivity appeared to increase only modestly with micropore surface area for ZSM-5 catalysts not including an additional transition metal. For a low micropore surface area ZSM-5 catalyst, addition of a transition metal did not appear to provide a clear benefit in aromatics selectivity. However, for a catalyst according to the invention that included both a high micropore surface area and a transition metal (Zn in this example), a substantial increase in aromatics selectivity appeared to be achieved. It is noted that the maximum aromatic yields for H-ZSM-5 and Zn/H-ZSM-5 catalysts were achieved on a small ZSM-5 crystal.

For the data in Table 2, the effects of micropore surface area on aromatic yields from methanol conversion are shown for catalysts corresponding to self-bound H-ZSM-5 and Zn-modified H-ZSM-5 catalysts. The methanol conversion reaction used to generate the results in Table 2 was performed at about 500° C., about 13.5 psig (about 95 kPag) CH$_3$OH, about 1.5 psig (about 11 kPag) H$_2$O (inlet pressures), and about 20 WHSV (g-CH$_3$OH g-catalyst$^{-1}$ h$^{-1}$). These conditions appeared to result in substantially complete conversion of the methanol in the feed.

TABLE 2

Micropore Surface Area and Metals Content versus Aromatics Yield

| Catalyst | Si/Al$_2$ | Micropore Surface Area (m$^2$/g) | Zn content (wt %) | Aromatics (wt %) in hydrocarbon product |
|---|---|---|---|---|
| H-ZSM-5 | ~60 | >350 | — | ~29 |
| H-ZSM-5 | ~60 | <340 | — | ~27 |
| H-ZSM-5 | ~60 | <250 | — | ~25 |
| Zn/H-ZSM-5 | ~60 | >350 | ~0.93 | ~57 |
| Zn/H-ZSM-5 | ~60 | <250 | ~0.86 | ~22 |

Example 3—Combined Aromatics and Olefins Yield and Residual Carbon

Both aromatics and olefins are considered higher value products than paraffins in methanol conversion. Table 3 shows the combined aromatics and olefin (A+O) selectivity as well as the residual carbon deposited on the catalyst (measured post-reaction, ex-situ via a thermogravimetric method) for various H-ZSM-5 and Zn/H-ZSM-5 catalysts. In Table 3, the wt % of coke or residual carbon is expressed as a wt % relative to the weight of catalyst. The residual carbon present on the ZSM-5 catalysts after performing methanol conversion can be an indicator of how rapidly such catalysts will deactivate (via coking) during extended periods of methanol conversion.

For catalysts without an additional transition metal, the A+O selectivity appeared similar for catalysts with micropore surface areas greater than about 250 m$^2$/g at a given Si/Al$_2$ ratio. However, coking seemed to be exacerbated for the H-ZSM-5 catalysts with micropore surface area less than about 340 m$^2$/g. The amount of coking also appeared to increase for H-ZSM-5 catalysts with a ratio of Si to Al$_2$ of 30 or less. For catalysts including a transition metal, but with a micropore surface area less than the about 340 m$^2$/g for a catalyst according to the invention, increased coking may be related to a low availability of reaction sites for forming aromatics relative to acidic reaction sites that can cause, for example, cracking. Similarly, for catalysts including a transition metal but with a low diffusivity, the low diffusivity can indicate an increased diffusion time (potentially equivalent to an increased diffusion length) for compounds trying to exit a catalyst pore. An increase in diffusion length and/or diffusion time for compounds in the zeolite catalysts could lead to further unsaturation of hydrogen-deficient species (and coking) before such species can escape the zeolite pores.

The presence of Zn on H-ZSM-5 catalysts with a micropore surface area greater than about 350 m$^2$/g appeared to increase the A+O selectivity to about 81%, compared to an about 49% A+O selectivity for H-ZSM-5 without a transition metal. It is noted that the A+O selectivity for a catalyst with Zn on H-ZSM-5 with a lower micropore surface area was measured at about 71%. Although the combined A+O yield seemed high, as shown previously in Example 2, the aromatics portion of the combined A+O yield appeared to be only about 30 wt %, meaning that the majority of the A+O selectivity was likely due to production of olefins. While olefins can be a desirable product relative to paraffins, aromatics can be a still more desirable product.

Table 3 shows aromatic plus olefin (A+O) selectivity and residual carbon remaining on catalyst after reaction of a methanol feed in the presence of H-ZSM-5 and Zn-modified H-ZSM-5 catalysts. The reaction conditions for generating the results in Table 3 included a temperature of about 500° C., an inlet methanol partial pressure of about 13.5 psig (about 95 kPag) CH$_3$OH, an inlet water partial pressure of about 1.5 psig (about 11 kPag) H$_2$O, and a space velocity of about 20 WHSV (g-CH$_3$OH g-catalyst$^{-1}$ h$^{-1}$). The reaction conditions appeared to be sufficient to cause substantially complete conversion of the methanol in the feed.

TABLE 3

Aromatics Plus Olefin Yield and Residual Carbon

| Catalyst | Si/Al$_2$ | Micropore Surface Area (m$^2$/g) | Aromatics plus olefins (wt %) in hydrocarbon product | Residual carbon (wt %) after reaction | 2,2-DMB diffusivity (sec$^{-1}$) |
|---|---|---|---|---|---|
| H-ZSM-5 | ~60 | >350 | ~49 | ~0.5 | ~4.9 × 10$^{-2}$ |
| H-ZSM-5 | ~30 | >350 | ~45 | ~5.1 | ~1.7 × 10$^{-2}$ |
| H-ZSM-5 | ~60 | <340 | ~49 | ~1.2 | <N/A> |
| H-ZSM-5 | ~30 | <340 | ~45 | ~6.1 | ~3.1 × 10$^{-3}$ |
| Zn/H-ZSM-5 | ~60 | >350 | ~81 | ~0.1 | ~1.5 × 10$^{-1}$ |
| Zn/H-ZSM-5 | ~60 | <250 | ~71 | ~6.0 | ~7.7 × 10$^{-2}$ |

As shown in Table 3, various factors can result in increased coke formation on a catalyst. In order to avoid coke formation, a combination of a moderate silicon to aluminum ratio, a sufficiently high micropore surface area, and a sufficiently high 2,2-DMB diffusivity can lead to reduced coke formation on a catalyst. Note that diffusivity data was not obtained for the process run corresponding to row 3 in Table 3.

Example 4—Alumina Binders

Forming a bound zeolite catalyst can have a variety of impacts on the catalyst, including a potential reduction of the micropore surface area for the catalyst. Table 4 shows the impact of different catalyst binders on the activity for production of aromatics and olefins (A+O) for Zn/H-ZSM-5 catalysts.

For the process runs in Table 4, similar samples of H-ZSM-5 crystals were used to form self-bound and alumina-bound catalysts with the binder contents shown in Table 4. These catalysts were then impregnated (via incipient wetness) with zinc to form the Zn/H-ZSM-5 catalysts with the zinc contents shown in Table 4. The catalysts were also characterized to determine micropore surface area and mesopore surface area. As shown in Table 4, the alumina bound catalysts were found to exhibit lower micropore surface areas than a self-bound catalyst made using the same type of H-ZSM-5 zeolite crystals. However, using an alumina binder with a surface area of less than about 200 m$^2$/g appeared to result in a catalyst with a micropore surface area of about 315 m$^2$/g and a corresponding mesopore surface area of less than about 85 m$^2$/g. This represents a combined micropore and mesopore surface area of almost 400 m$^2$/g.

By contrast, use of a higher surface area alumina binder appeared to result in comparable micropore and mesopore surface areas, with the combined micropore and mesopore surface area being less than about 380 m$^2$/g. As shown in Table 4, this small difference in combined micropore and mesopore surface area appeared to result in a ~4 wt % increase in the amount of aromatics plus olefins generated by the catalyst having the low surface area alumina binder. The catalysts in Table 4 were tested for methanol conversion at a temperature of about 500° C., a total inlet pressure of about 15 psig (about 110 kPag) (about 13.5 psig/about 95 kPag CH$_3$OH, about 1.5 psig/about 11 kPag H$_2$O), and a space velocity of about 20 WHSV (g-CH$_3$OH g-catalyst$^{-1}$ h$^{-1}$). The reaction conditions appeared to result in substantially complete conversion of the methanol in the feed. It is noted that the Si to Al$_2$ ratio for the catalysts in Table 4 was about 60.

TABLE 4

Alumina Binders

| Catalyst | Binder type | Binder content, wt % | Zn content, wt % (based on zeolite) | Aromatics + Olefins (wt % of HC) | Catalyst Micropore Surface Area (m$^2$ g$^{-1}$) | Catalyst Mesopore Surface Area (m$^2$ g$^{-1}$) |
|---|---|---|---|---|---|---|
| Zn/H-ZSM-5 | Self-bound | 0 | ~0.93 | ~81 | ~380 | n/a |
| Zn/H-ZSM-5 | Al$_2$O$_3$ | ~20 | ~0.98 | ~73 | ~315 | ~82 |
| Zn/H-ZSM-5 | Al$_2$O$_3$ | ~35 | ~0.92 | ~69 | ~192 | ~188 |

Example 5—Comparison of Group 12 (Group IIB) Transition Metals

Table 4 demonstrates the advantage of Zn or Cd addition to self-bound ZSM-5 catalysts, as compared to equivalent self-bound ZSM-5 without modification by inclusion of a transition metal. The unmodified and transition metal-modified catalysts were tested for methanol conversion at a temperature of about 500° C., a total inlet pressure of about 15 psig (about 110 kPag) (about 13.5 psig/about 95 kPag CH$_3$OH, about 1.5 psig/about 11 kPag H$_2$O), and a space velocity of about 20 WHSV (g-CH$_3$OH g-catalyst$^{-1}$ h$^{-1}$). The reaction conditions appeared to result in substantially complete conversion of the methanol in the feed.

TABLE 5

Comparison of Group 12 Transition Metals

| Example | Si/Al$_2$ | Micropore Surface Area (m$^2$/g) | Metal promoter | Metal content (wt %) | Aromatics (wt. %) in product |
|---|---|---|---|---|---|
| 1 | ~60 | >350 | — | — | ~30 |
| 2 | ~60 | >350 | Zn | ~0.93 | ~57 |
| 3 | ~60 | >350 | Cd | ~0.75 | ~54 |

Example 6—Aromatics Yield Relative to Liquid Product Yield

The methanol to aromatics conversion examples shown in Tables 1-5 correspond to reaction conditions with high space velocities of methanol feed relative to the amount of catalyst. In a commercial setting, lower space velocities are likely to be preferred, such as space velocities (WHSV) between about 0.1 and about 5.0 g-CH$_3$OH g-catalyst$^{-1}$ h$^{-1}$. Table 6 shows an example of hydrocarbon product liquid yields as well as the aromatic fraction of such yields for an H-ZSM-5 catalyst and a corresponding Zn/H-ZSM-5 catalyst at a WHSV of ~2, representing more typical commercial operating conditions for a reactor. The liquid yield corresponds to the yield of C5+ compounds. The results in Table 6 were generated at a temperature of about 450° C. and a total inlet pressure of about 15 psig (about 110 kPag). It is noted that for this example, the feed was substantially composed of methanol (trace amounts of water may have been present). The catalysts correspond to catalysts with a micropore surface area of greater than about 350 m$^2$/g.

TABLE 6

Aromatics Yield versus Liquid Yield

| Catalyst | MeOH conversion/% | Liquid yield/wt % of product | Aromatics yield/wt % of product |
| --- | --- | --- | --- |
| H-ZSM-5 | 99.8 | 48.6 | 40.4 |
| Zn/H-ZSM-5 | 99.8 | 64.9 | 60.3 |

As shown in Table 6, at a WHSV of less than about 5, the aromatics yield for both the catalysts with and without additional transition metal appeared different from the liquid yield by about 10 wt % or less, indicating that a relatively low weight percentage of paraffins were being generated. As shown in Table 6, addition of the additional transition metal not only appeared to improve the aromatics yield to greater than about 60 wt %, but also the difference between the aromatics yield and the liquid yield appeared to be less than 5 wt %. Thus, the additional transition metal not only appeared to improve the aromatics yield, but also apparently reduced the yield of the less desirable C5+ paraffin type compounds.

Example 7—Regeneration of Catalyst

ZSM-5 catalysts can suffer both reversible and irreversible deactivation via coking, and steaming, respectively, during methanol conversion. The increased selectivity to aromatic products on Zn/H-ZSM-5 catalysts could promote the formation of polynuclear arene species, which are known precursors to coke. Regeneration of Zn/H-ZSM-5 self-bound catalysts was performed by treating the spent catalyst in air to about 850° F. (about 454° C.). Table 7 shows the Zn content and the aromatic selectivity of fresh and regenerated Zn/H-ZSM-5 samples. The regenerated Zn/H-ZSM-5 sample appeared to regain ~90+% of the selectivity to aromatics, compared to the fresh sample. The catalysts were tested for methanol conversion at a temperature of about 500° C., a total pressure of about 15 psig (about 110 kPag) (about 13.5 psig/about 95 kPag CH$_3$OH, about 1.5 psig/about 11 kPag H$_2$O), and a space velocity of about 20 WHSV (g-CH$_3$OH g-catalyst$^{-1}$ h$^{-1}$). The reaction conditions appeared to result in substantially complete conversion of the methanol in the feed.

TABLE 7

Catalyst Activity after Regeneration

| Catalyst | Si/Al$_2$ | Micropore Surface Area (m$^2$/g) | Zn content (wt %) | Aromatics (wt %) in product |
| --- | --- | --- | --- | --- |
| Zn/H-ZSM-5 (fresh) | ~60 | >350 | ~0.93 | ~57 |
| Zn/H-ZSM-5 (regen) | ~60 | >350 | ~0.93 | ~52 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A catalyst composition comprising a zeolite comprising ZSM-5, an alumina binder, and a Group 12 transition metal selected from the group consisting of Zn, Cd, or a combination thereof,
   the zeolite having a silicon to aluminum ratio of at least about 10,
   the zeolite having a micropore surface area of at least about 340 m$^2$/g,
   the catalyst composition comprising about 80 wt % or less of the binder based on a total weight of the catalyst composition, and
   the catalyst composition having a micropore surface area of at least about 290 m$^2$/g, a molar ratio of Group 12 transition metal to aluminum of about 0.1 to about 1.3, and at least one of:
   (a) a mesopore surface area of about 20 m$^2$/g to about 120 m$^2$/g;
   (b) a diffusivity for 2,2-dimethylbutane of greater than about 1×10$^{-2}$ sec$^{-1}$ when measured at a temperature of 120° C. and a 2,2-dimethylbutane pressure of 60 torr (about 8 kPa); and
   (c) a combined micropore surface area and mesopore surface area of at least about 380 m$^2$/g.

2. The catalyst composition of claim 1, wherein the binder has a surface area of about 200 m$^2$/g or less.

3. The catalyst composition of claim 1, wherein the catalyst composition comprises from about 5 wt % to about 40 wt % binder based on the total weight of the catalyst composition.

4. The catalyst composition of claim 1, wherein the zeolite has a microporous surface area of at least about 350 m$^2$/g.

5. The catalyst composition of claim 1, wherein the catalyst composition has a diffusivity for 2,2-dimethylbutane of greater than about 1.25×10$^{-2}$ sec$^{-1}$ when measured at a temperature of about 120° C. and a 2,2-dimethylbutane pressure of about 60 torr (about 8 kPa).

6. The catalyst composition of claim 1, wherein the catalyst composition has a mesopore surface area of greater than about 30 m$^2$/g.

7. The catalyst composition of claim 1, wherein the catalyst composition has a combined micropore surface area and mesopore surface area of at least about 390 m$^2$/g.

8. The catalyst composition of claim 1, wherein the zeolite has a constraint index of about 1 to about 12.

9. The catalyst composition of claim 1, wherein the zeolite further comprises ZSM-11, a zeolite having an MFI framework, a zeolite having an MEL framework, or a combination thereof.

10. The catalyst composition of claim 1, wherein the zeolite further comprises ZSM-11.

11. The catalyst composition of claim 1, wherein the silicon to aluminum molar ratio of the zeolite is from about 20 to about 100.

12. The catalyst composition of claim 1, wherein the amount of Group 12 transition metal is about 0.1 wt % to about 20 wt % of the total catalyst composition.

13. The catalyst composition of claim 1, wherein the catalyst composition has a mesopore surface area of about 20 $m^2/g$ to about 120 $m^2/g$, a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa), and a combined micropore surface area and mesopore surface area of at least about 380 $m^2/g$.

14. The catalyst composition of claim 1, wherein the catalyst composition has an alpha value of at least about 10.

15. A catalyst composition comprising a zeolite comprising ZSM-5, an alumina binder, and a Group 12 transition metal selected from the group consisting of Zn, Cd, or a combination thereof,
the zeolite having a silicon to aluminum ratio of at least about 20,
the zeolite having a micropore surface area of at least about 340 $m^2/g$,
the catalyst composition comprising about 50 wt % or less of the binder based on a total weight of the catalyst composition, and
the catalyst composition having a micropore surface area of at least about 290 $m^2/g$, a molar ratio of Group 12 transition metal to aluminum of about 0.1 to about 1.3, a mesopore surface area of about 20 $m^2/g$ to about 120 $m^2/g$, a diffusivity for 2,2-dimethylbutane of greater than about $1 \times 10^{-2}$ $sec^{-1}$ when measured at a temperature of about 120° C. and a 2,2-dimethylbutane pressure of about 60 torr (about 8 kPa), and a combined micropore surface area and mesopore surface area of at least about 380 $m^2/g$.

16. The catalyst composition of claim 1, wherein the catalyst composition has a microporous surface area of at least about 310 $m^2/g$.

* * * * *